United States Patent
Belalcazar

(10) Patent No.: US 7,890,163 B2
(45) Date of Patent: Feb. 15, 2011

(54) METHOD AND APPARATUS FOR DETECTING FIBRILLATION USING CARDIAC LOCAL IMPEDANCE

(75) Inventor: Andres Belalcazar, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 690 days.

(21) Appl. No.: 11/550,923

(22) Filed: Oct. 19, 2006

(65) Prior Publication Data
US 2008/0097539 A1  Apr. 24, 2008

(51) Int. Cl.
*A61B 5/053* (2006.01)
(52) U.S. Cl. .................................. 600/547
(58) Field of Classification Search ............. 607/17, 607/18, 24, 4, 5, 6, 14; 600/547
See application file for complete search history.

(56) References Cited

U.S. PATENT DOCUMENTS

| | | | |
|---|---|---|---|
| 4,202,340 A * | 5/1980 | Langer et al. ............... | 607/5 |
| 5,058,583 A | 10/1991 | Geddes et al. | |
| 5,179,946 A * | 1/1993 | Weiss ......................... | 607/4 |
| 5,385,576 A * | 1/1995 | Noren et al. ................ | 607/6 |
| 6,070,100 A * | 5/2000 | Bakels et al. ................ | 607/9 |
| 6,223,082 B1 * | 4/2001 | Bakels et al. ................ | 607/17 |
| 6,278,894 B1 * | 8/2001 | Salo et al. ................... | 600/547 |
| 6,871,088 B2 * | 3/2005 | Chinchoy .................... | 600/510 |
| 7,190,996 B2 | 3/2007 | Jarverud | |
| 7,203,541 B2 | 4/2007 | Sowelam et al. | |
| 7,440,803 B2 * | 10/2008 | Ni et al. ...................... | 607/9 |
| 7,640,058 B2 | 12/2009 | Lang | |
| 2002/0002389 A1 * | 1/2002 | Bradley et al. .............. | 607/8 |
| 2003/0199955 A1 | 10/2003 | Struble et al. | |
| 2005/0038481 A1 * | 2/2005 | Chinchoy et al. ........... | 607/17 |
| 2005/0096704 A1 | 5/2005 | Freeberg | |
| 2005/0154421 A1 | 7/2005 | Ousdigian et al. | |
| 2006/0293714 A1 | 12/2006 | Salo et al. | |
| 2007/0005114 A1 * | 1/2007 | Salo et al. ................... | 607/17 |
| 2007/0066905 A1 | 3/2007 | Zhang | |
| 2008/0234773 A1 | 9/2008 | Ni et al. | |

OTHER PUBLICATIONS

Griesbach, L., et al., "Clinical Performance of Automatic Closed-Loop Stimulation Systems.", *Pacing and Clinical Electrophysiology*, 26(7 Pt 1), (J2003), 1432-1437.
"International Application Serial No. PCT/US2008/003720, Written Opinion mailed Aug. 19, 2008", 6 pgs.
"U.S. Appl. No. 11/690,700, Non-Final Office Action mailed Dec. 30, 2009", 7 pgs.
"U.S. Appl. No. 11/690,700, Response filed Mar. 30, 2010 to Non Final Office Action mailed Dec. 30, 2009", 14 pgs.
"U.S. Appl. No. 11/690,700 Notice of Allowance mailed Jul. 20, 2010", 6 pgs.

* cited by examiner

*Primary Examiner* — Niketa I Patel
*Assistant Examiner* — Hiba El-Kaissi
(74) *Attorney, Agent, or Firm* — Schwegman, Lundberg & Woessner, P.A.

(57) ABSTRACT

A cardiac rhythm management (CRM) system detects tachyarrhythmia using cardiac local impedance indicative of cardiac local wall motion. A cardiac local impedance signal indicative of an impedance of a cardiac region is sensed by using a pair of bipolar electrodes placed in that cardiac region. Tachyarrhythmia such as VF is detected by analyzing one or more cardiac local impedance signals sensed in one or more cardiac regions.

25 Claims, 9 Drawing Sheets

METHOD AND APPARATUS FOR DETECTING FIBRILLATION USING CARDIAC LOCAL IMPEDANCE

TECHNICAL FIELD

This document relates generally to cardiac rhythm management (CRM) systems and particularly to an anti-tachyarrhythmia system that detects fibrillation using cardiac local impedance indicative of cardiac local wall motion.

BACKGROUND

Tachyarrhythmias are abnormal heart rhythms characterized by a rapid heart rate. Tachyarrhythmias generally include supraventricular tachyarrhythmia (SVT, including atrial tachyarrhythmia, AT) and ventricular tachyarrhythmia (VT). Fibrillation is a form of tachyarrhythmia further characterized by an irregular heart rhythm. In a normal heart, the sinoatrial node, the heart's predominant natural pacemaker, generates electrical impulses, called action potentials, that propagate through an electrical conduction system to the atria and then to the ventricles of the heart to excite the myocardial tissues. The atria and ventricles contract in the normal atrioventricular sequence and synchrony to result in efficient blood-pumping functions indicated by a normal hemodynamic performance. VT occurs when the electrical impulses propagate along a pathologically formed self-sustaining conductive loop within the ventricles or when a natural pacemaker in a ventricle usurps control of the heart rate from the sinoatrial node. When the atria and the ventricles become dissociated during VT, the ventricles may contract before they are properly filed with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Cardioversion and defibrillation are used to terminate most tachyarrhythmias, including AT, VT, and VF. An implantable cardioverter/defibrillator (ICD) is a CRM device that delivers an electric shock to terminate a detected tachyarrhythmia episode by depolarizing the entire myocardium simultaneously and rendering it refractory. Another type of electrical therapy for tachyarrhythmia is anti-tachyarrhythmia pacing (ATP). In ATP, the heart is competitively paced in an effort to interrupt the reentrant loop causing the tachyarrhythmia. An exemplary ICD includes ATP and defibrillation capabilities so that ATP is delivered to the heart when a non-fibrillation VT is detected, while a defibrillation shock is delivered when VF occurs.

The efficacy of cardioversion, defibrillation, and ATP in terminating tachyarrhythmia depends on the type and origin of the tachyarrhythmia. An unnecessary therapy delivered during a non-life-threatening tachyarrhythmia episode may cause substantial pain in the patient and reduces the longevity of the ICD while providing the patient with little or no benefit. On the other hand, a necessary therapy withheld during a life-threatening tachyarrhythmia episode may result in irreversible harm to the patient, including death. For these and other reasons, there is a need for accurate tachyarrhythmia detection that ensures patient safety while reducing unnecessary delivery of anti-tachyarrhythmia therapy.

SUMMARY

A CRM system detects tachyarrhythmia using cardiac local impedance indicative of cardiac local wall motion. A cardiac local impedance signal indicative of an impedance of a cardiac region is sensed by using a pair of bipolar electrodes placed in that cardiac region. Tachyarrhythmia such as VF is detected by analyzing one or more cardiac local impedance signals sensed in one or more cardiac regions.

In one embodiment, a CRM system includes an implantable lead and an implantable medical device. The implantable lead includes a proximal end, a distal end, and an elongate lead body coupled between the proximal end and the distal end. The proximal end is to be coupled to the implantable medical device. The distal end is to be placed in the heart and includes a pair of impedance sensing electrodes for sensing a cardiac local impedance signal. The implantable medical device includes an impedance sensing circuit and an impedance-based tachyarrhythmia detector. The impedance sensing circuit senses the cardiac local impedance signal using the pair of impedance sensing electrodes. The impedance-based tachyarrhythmia detector detects a predetermined-type tachyarrhythmia using the cardiac local impedance signal.

In one embodiment, a method for detecting tachyarrhythmia is provided. A cardiac local impedance signal is sensed using a pair of impedance sensing electrodes at a distal end of an implantable lead. A predetermined-type tachyarrhythmia is detected using the cardiac local impedance signal.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
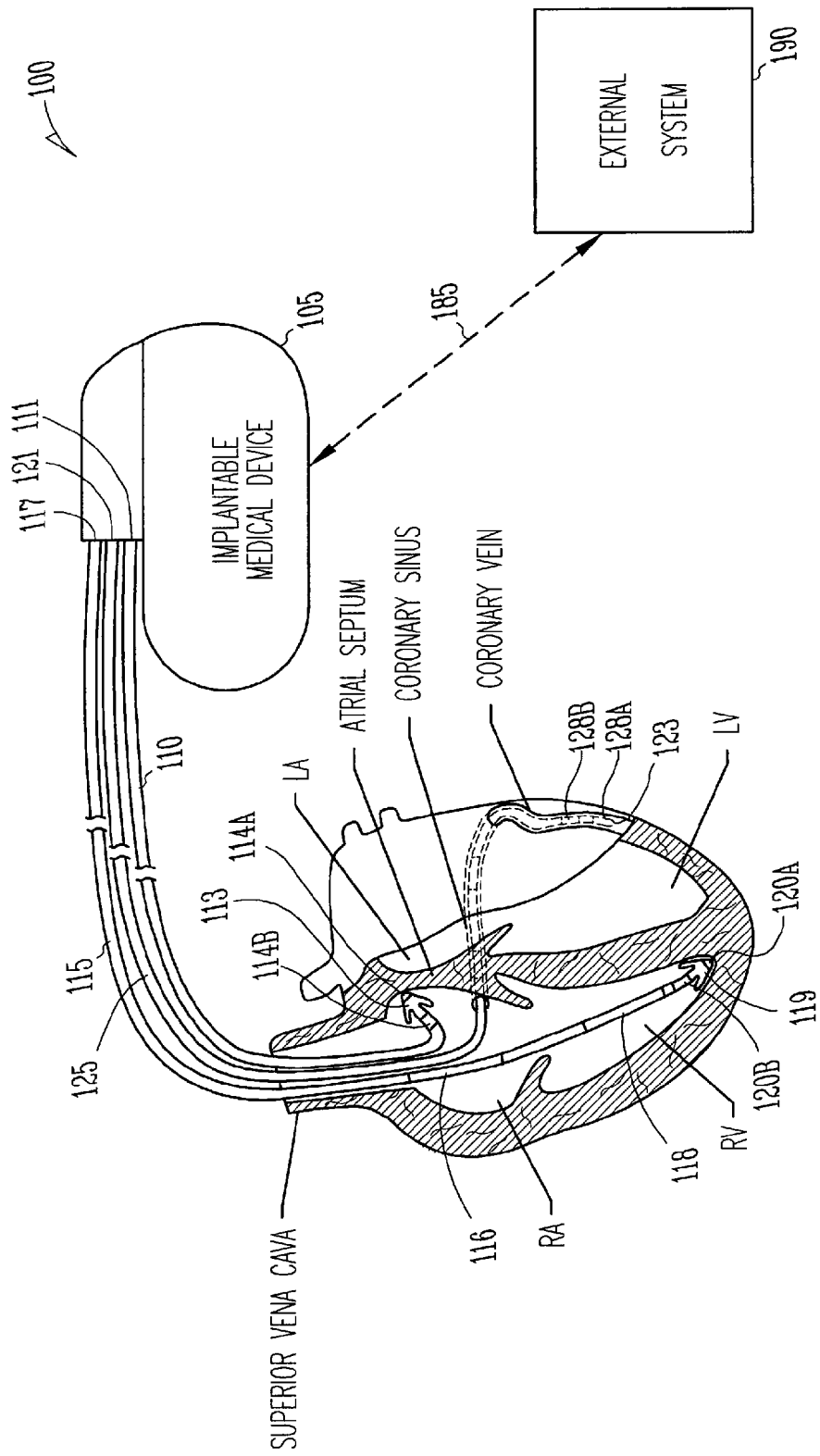
FIG. 1 is an illustration of an embodiment of a CRM system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

This document discusses a CRM system that detects tachyarrhythmia episodes using cardiac local impedance indicative of cardiac local wall motion. A tachyarrhythmia episode is detected by detecting one or more abnormalities in the mechanical activities of the heart. A cardiac local impedance signal indicative of a cardiac local impedance of a cardiac region is sensed by bipolar electrodes, such as bipolar electrodes on a pacing or defibrillation lead, placed in that cardiac region. Tachyarrhythmia such as VF is detected by analyzing one or more cardiac local impedance signals sensed in one or more cardiac regions, or one or more cardiac local impedance derivative signals each indicative of the rate of change in one of the one or more cardiac local impedances. For example, VF is detected by analyzing a motion pattern of a cardiac region indicated by the cardiac local impedance signal sensed from that cardiac region, or by analyzing the synchrony of local wall motions in two cardiac regions indicated by the cardiac local impedance signals sensed from those two cardiac regions.

In this document, an "impedance signal" or "Z" includes a signal indicative of impedance. In one embodiment, the impedance signal is produced as a ratio of a sensed voltage to a current delivered for impedance sensing. In another embodiment, the impedance is a sensed voltage signal indicative of impedance, for example, when the current delivered for impedance sensing is from a constant-current source. An "impedance derivative signal" or "dZ/dT" indicates a rate of change in the impedance signal. For example, a "cardiac local impedance signal (Z)" includes a signal indicative of a cardiac local (regional) impedance, a "cardiac local impedance derivative signal (dZ/dT)" in indicates a rate of change in the cardiac local impedance, a "left ventricular (LV) local impedance signal (LVZ)" includes a signal indicative of an LV local (regional) impedance, an "LV local impedance derivative signal (dZ/dT)" in indicates a rate of change in the LV local impedance signal, a "right ventricular (RV) local impedance signal (RVZ)" includes a signal indicative of an RV local (regional) impedance, an "RV local impedance derivative signal (dZ/dT)" in indicates a rate of change in the RV local impedance.

As discussed in this document, the cardiac local impedance is indicative of cardiac local wall motion, which includes thickening of the cardiac wall due to systolic contraction and reorientation of impedance sensing electrodes relative to the contracting myocardium. The cardiac local impedance is also affected by displacement of blood in the myocardium due to its contraction.

FIG. 1 is an illustration a CRM system 100 and portions of an environment in which system 100 operates. CRM system 100 includes an implantable medical device 105 that is electrically coupled to a heart through implantable leads 110, 115, and 125. An external system 190 communicates with implantable medical device 105 via a telemetry link 185.

Implantable medical device 105 includes a hermetically sealed can housing an electronic circuit that senses physiological signals and delivers therapeutic electrical pulses. The hermetically sealed can also functions as an electrode for sensing and/or pulse delivery purposes. In one embodiment, implantable medical device 105 includes an arrhythmia detection circuit that detects tachyarrhythmias and determines whether a therapy is to be delivered from implantable medical device 105. For example, if VF is detected, implantable medical device 105 delivers a defibrillation therapy. In one embodiment, implantable medical device 105 is an ICD with cardiac pacing capabilities. In another embodiment, in addition to a pacemaker and a cardioverter/defibrillator, implantable medical device 105 further includes one or more of other monitoring and/or therapeutic devices such as a neural stimulator, a drug delivery device, and a biological therapy device.

Lead 110 is an right atrial (RA) pacing lead that includes an elongate lead body having a proximal end 111 and a distal end 113. Proximal end 111 is coupled to a connector for connecting to implantable medical device 105. Distal end 113 is configured for placement in the RA in or near the atrial septum. Lead 110 includes an RA tip electrode 114A, and an RA ring electrode 114B. RA electrodes 114A and 114B are incorporated into the lead body at distal end 113 for placement in or near the atrial septum, and are each electrically coupled to implantable medical device 105 through a conductor extending within the lead body. RA tip electrode 114A, RA ring electrode 114B, and/or the can of implantable medical device 105 allow for sensing an RA electrogram indicative of RA depolarizations and delivering RA pacing pulses. In one embodiment, RA electrodes 114A and 114B function as a pair of RA impedance sensing electrodes for sensing an RA local impedance signal. The distance between RA tip electrode 114A and RA ring electrode 114B is in a range of approximately 2 millimeters to 20 millimeters, with approximately 5 millimeters being a specific example.

Lead 115 is a right ventricular (RV) pacing-defibrillation lead that includes an elongate lead body having a proximal end 117 and a distal end 119. Proximal end 117 is coupled to a connector for connecting to implantable medical device 105. Distal end 119 is configured for placement in the RV. Lead 115 includes a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava. Defibrillation electrode 118 is incorporated into the lead body near distal end 119 for placement in the RV. RV electrodes 120A and 120B are incorporated into the lead body at distal end 119. Electrodes 116, 118, 120A, and 120B are each electrically coupled to implantable medical device 105 through a conductor extending within the lead body. Proximal defibrillation electrode 116, distal defibrillation electrode 118, and/or the can of implantable medical device 105 allow for delivery of cardioversion/defibrillation pulses to the heart. RV tip electrode 120A, RV ring electrode 120B, and/or the can of implantable medical device 105 allow for sensing an RV electrogram indicative of RV depolarizations and delivering RV pacing pulses. In one embodiment, RV electrodes 120A and 120B function as a pair of RV impedance sensing electrodes for sensing an RV local impedance signal. The distance between RV tip electrode 120A and RV ring electrode 120B is in a range of approximately 2 millimeters to 20 millimeters, with approximately 8 millimeters being a specific example.

Lead 125 is a left ventricular (LV) coronary pacing lead that includes an elongate lead body having a proximal end 121 and a distal end 123. Proximal end 121 is coupled to a connector for connecting to implantable medical device 105. Distal end 123 is configured for placement in the coronary vein. Lead 125 includes an LV tip electrode 128A and an LV ring electrode 128B. The distal portion of lead 125 is configured for placement in the coronary sinus and coronary vein such that LV electrodes 128A and 128B are placed in the coronary vein. LV electrodes 128A and 128B are incorporated into the lead body at distal end 123 and each electrically coupled to implantable medical device 105 through a conductor extending within the lead body. LV tip electrode 128A, LV ring electrode 128B, and/or the can of implantable medical device 105 allow for sensing an LV electrogram indicative of LV depolarizations and delivering LV pacing pulses. In one embodiment, LV electrodes 128A and 128B function as a pair of LV impedance sensing electrodes for sensing an LV local impedance signal. The distance between LV tip electrode 128A and LV ring electrode 128B is in a range of approximately 2 millimeters to 40 millimeters, with approximately 11 millimeters being a specific example.

In various embodiments, one or more pairs of impedance sensing electrodes are used, with each pair configured to sense a cardiac local impedance signal. The impedance sensing electrodes of each pair are spaced to sense an impedance that is indicative of local wall motion in a cardiac region. Each impedance sensing electrode may also be used for sensing an electrogram and/or delivering pacing or defibrillation pulses. The lead configuration including RA lead 110, RV lead 115, and LV lead 125 is illustrated in FIG. 1 as an example. Other lead configurations may be used, depending on monitoring and therapeutic requirements. For example, additional leads may be used to provide access to additional cardiac regions, and leads 110, 115, and 125 may each include more or fewer electrodes along the lead body at, near, and/or distant from the distal end, depending on specified monitoring and therapeutic needs. External system 190 allows for programming of implantable medical device 105 and receives signals acquired by implantable medical device 105. In one embodiment, telemetry link 185 is an inductive telemetry link. In an alternative embodiment, telemetry link 185 is a far-field radio-frequency telemetry link. Telemetry link 185 provides for data transmission from implantable medical device 105 to external system 190. This may include, for example, transmitting real-time physiological data acquired by implantable medical device 105, extracting physiological data acquired by and stored in implantable medical device 105, extracting therapy history data stored in implantable medical device 105, and extracting data indicating an operational status of implantable medical device 105 (e.g., battery status and lead impedance). Telemetry link 185 also provides for data transmission from external system 190 to implantable medical device 105. This may include, for example, programming implantable medical device 105 to acquire physiological data, programming implantable medical device 105 to perform at least one self-diagnostic test (such as for a device operational status), programming implantable medical device 105 to run a signal analysis algorithm (such as an algorithm implementing the tachyarrhythmia detection method discussed in this document), and programming implantable medical device 105 to deliver pacing and/or cardioversion/defibrillation therapies.

The circuit of CRM system 100 may be implemented using a combination of hardware and software. In various embodiments, each element of implantable medical device 105 as illustrated in FIGS. 2-8, including its specific embodiments, may be implemented using an application-specific circuit constructed to perform one or more particular functions or a general-purpose circuit programmed to perform such function(s). Such a general-purpose circuit includes, but is not limited to, a microprocessor or portions thereof, a microcontroller or portions thereof, and a programmable logic circuit or portions thereof. For example, a "comparator" includes, among other things, an electronic circuit comparator constructed to perform the only function of comparing two or more signals or a portion of a general-purpose circuit driven by a code instructing that portion of the general-purpose circuit to perform the comparing.

Figure 2:
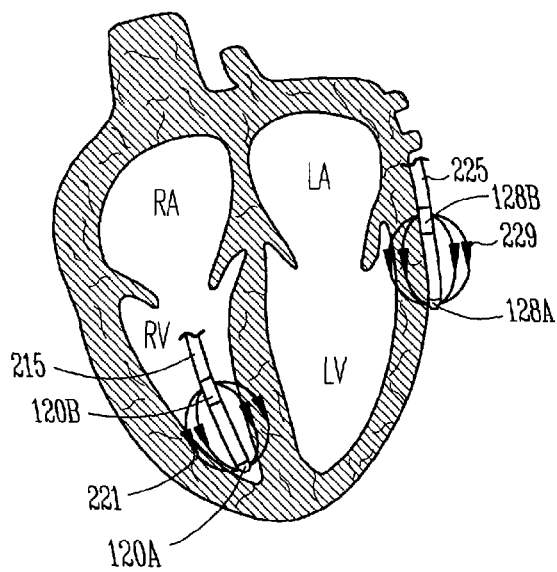
FIG. 2 is an illustration of an embodiment of cardiac local impedance sensing.

FIG. 2 is an illustration of an embodiment of cardiac local impedance sensing. A lead 215 represents portions of lead 115 including RV electrodes 120A and 120B function as a pair of RV impedance sensing electrodes. A lead 225 represents portions of lead 125 including LV electrodes 128A and 128B function as a pair of LV impedance sensing electrodes. RV electrodes 120A and 120B are used for injecting a current 221 and sensing the resulting voltage indicative of the RV local impedance. LV electrodes 128A and 128B are used for injecting a current 229 and sensing the resulting voltage indicative of the LV local impedance. The cardiac local impedance is sensed using two closely spaced impedance sensing electrodes (e.g., within 20 millimeters for the RA or RV, or within 40 millimeters for the LV) placed over or near the myocardium. In one embodiment, the distance between the two impedance sensing electrodes is within approximately 20 millimeters. The sensed cardiac local impedance signal is indicative of local motion and/or geometrical changes of the myocardial region in the vicinity of the impedance sensing electrodes.

In this document, an signal sensed or event detected using an RV lead such as lead 115 or 215 is referred to as an "RV" signal or an "RV" event, and an signal sensed or event detected using an LV lead such as lead 125 or 225 is referred to as an "LV" signal or an "LV" event. For example, when electrode 120A and 120B are used to deliver pacing pulse to the RV-LV septum to control LV activation, the cardiac local impedance sensed using these two electrodes are still referred to as an RV local impedance indicative of RV local motion. An "interventricular delay" between an RV event and an LV event includes a delay between an event detected using an RV lead such as lead 115 or 215 and an event detected using an LV lead such as lead 125 or 225.

Figure 3:
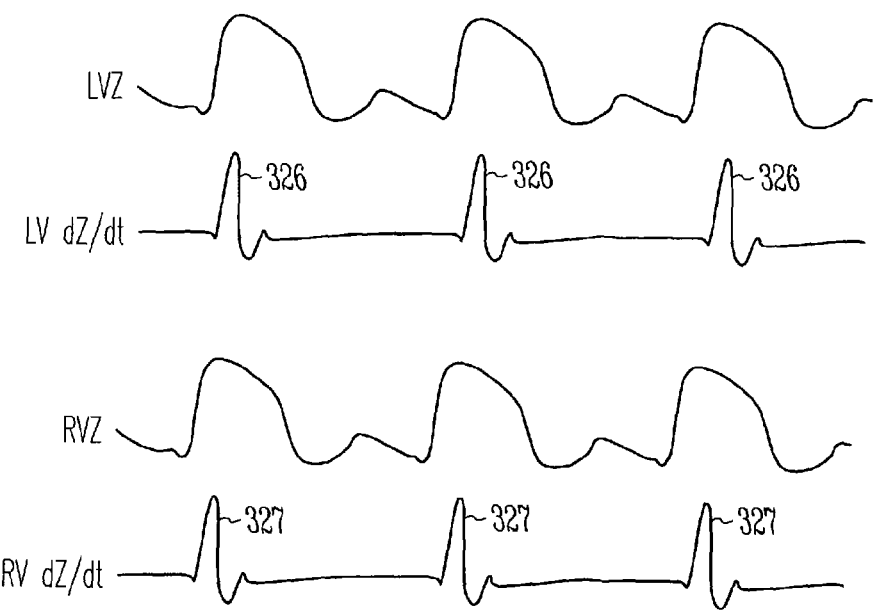
FIG. 3 is an illustration of examples of signals resulting from cardiac local impedance sensing.

FIG. 3 is an illustration of examples of signals resulting from cardiac local impedance sensing. The illustrated signals include an LV impedance signal (LVZ), an LV impedance derivative signal (LV dZ/dT), an RV impedance signal (RVZ), and an RV impedance derivative signal (RV dZ/dT), sensed during a regular cardiac rhythm. The LVZ represents an impedance signal sensed using LV electrodes 128A and 128B. The LV dZ/dT represents the rate of change in the LVZ. The RVZ represents an impedance signal sensed using RV electrodes 120A and 120B. The RV dZ/dT represents the rate of change in the RVZ. These signals and their uses are further discussed below. The LV dZ/dT includes LV impedance events 326. The RV dZ/dT includes RV impedance events 327. In one embodiment, such impedance events are each representative of a cardiac local wall motion during the systolic phase of each cardiac cycle. The LV impedance events each represent the LV local wall motion during the systolic phase of each cardiac cycle. The RV impedance events each represent the RV local wall motion during the systolic phase of each cardiac cycle. During a normal sinus rhythm or a tachycardia with a regular rhythm, such illustrated in FIG. 3, the LV and RV contract in synchrony, and the LV and RV impedance events during each cardiac cycle occur approximately simultaneously or within a limited interventricular delay.

Figure 4:
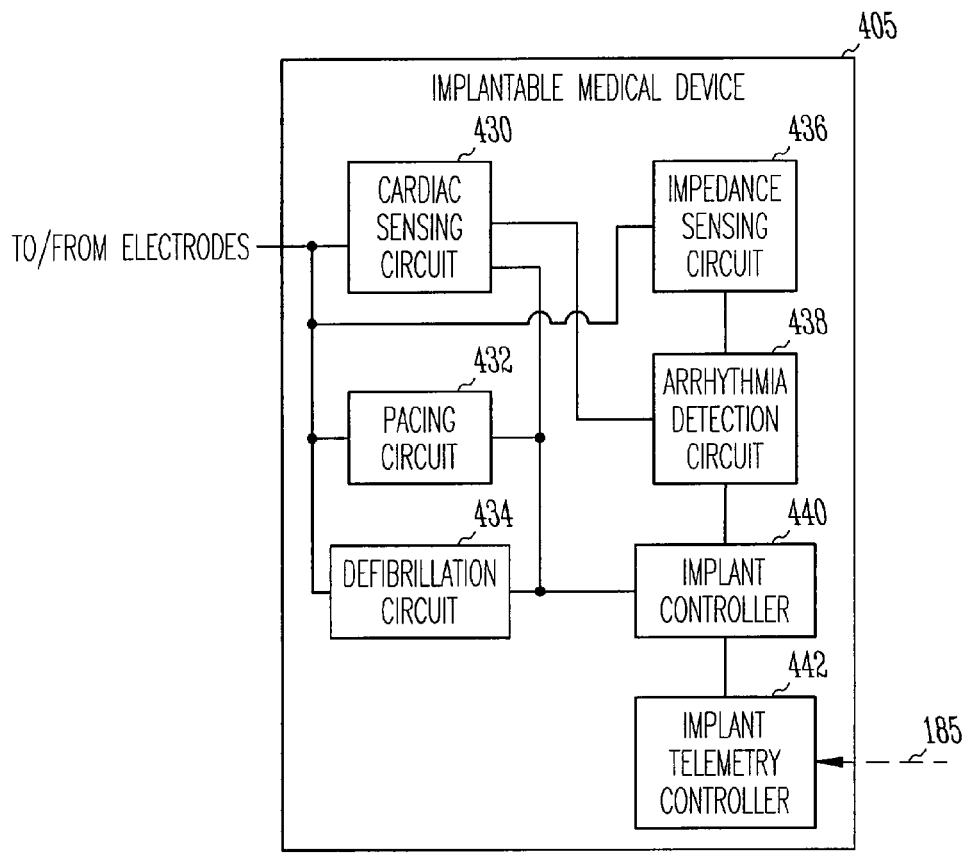
FIG. 4 is a block diagram illustrating an embodiment of an implantable medical device of the CRM system.

FIG. 4 is a block diagram illustrating an embodiment of an implantable medical device 405. Implantable medical device 405 is a specific embodiment of an implantable medical device 105 and includes a cardiac sensing circuit 430, a pacing circuit 432, a defibrillation circuit 434, an impedance sensing circuit 436, an arrhythmia detection circuit 438, an implant controller 440, and an implant telemetry circuit 442. Cardiac sensing circuit 430 senses one or more electrograms from the heart through electrodes such as those selected from RA electrodes 114A and 114B, RV electrodes 120A and 120B, LV electrodes 128A and 128B, and the can of implantable medical device 405. Pacing circuit 432 delivers pacing pulses to the heart through electrodes such as those selected from RA electrodes 114A and 114B, RV electrodes 120A and 120B, LV electrodes 128A and 128B, and the can of implantable medical device 405. Defibrillation circuit 434 delivers cardioversion/defibrillation pulses through electrodes such as those selected from defibrillation electrodes 116 and 118 and the can of implantable medical device 405. Impedance sensing circuit 436 produces one or more cardiac local impedance signals each by sensing a voltage across a pair of impedance sensing electrodes placed in a cardiac region. In one embodiment, impedance sensing circuit 436 produces each cardiac local impedance signal as the ratio of the sensed voltage to a current delivered for the impedance sensing. In another embodiment, impedance sensing circuit 436 produces each cardiac local impedance signal by isolating the signal component indicative of the cardiac local impedance from the sensed voltage, when the current delivered for the impedance sensing is from a constant-current source. Examples of the pair of impedance sensing electrodes include the pair of RA impedance sensing electrodes 114A and 114B, the pair of LV impedance sensing electrodes 128A and 128B, and the pair of RV impedance sensing electrodes 120A and 120B. Arrhythmia detection circuit 438 detects tachyarrhythmias using at least the sensed one or more cardiac local impedance signals. Implant controller 440 controls the operation of implantable medical device 405, including delivery of an anti-tachyarrhythmia therapy in response to the detection of tachyarrhythmia, such as the delivery of a ventricular defibrillation therapy in response to a detection of VF. Implant telemetry circuit 442 receives signals from, and transmits signals to, external system 190 via telemetry link 185.

Figure 5:
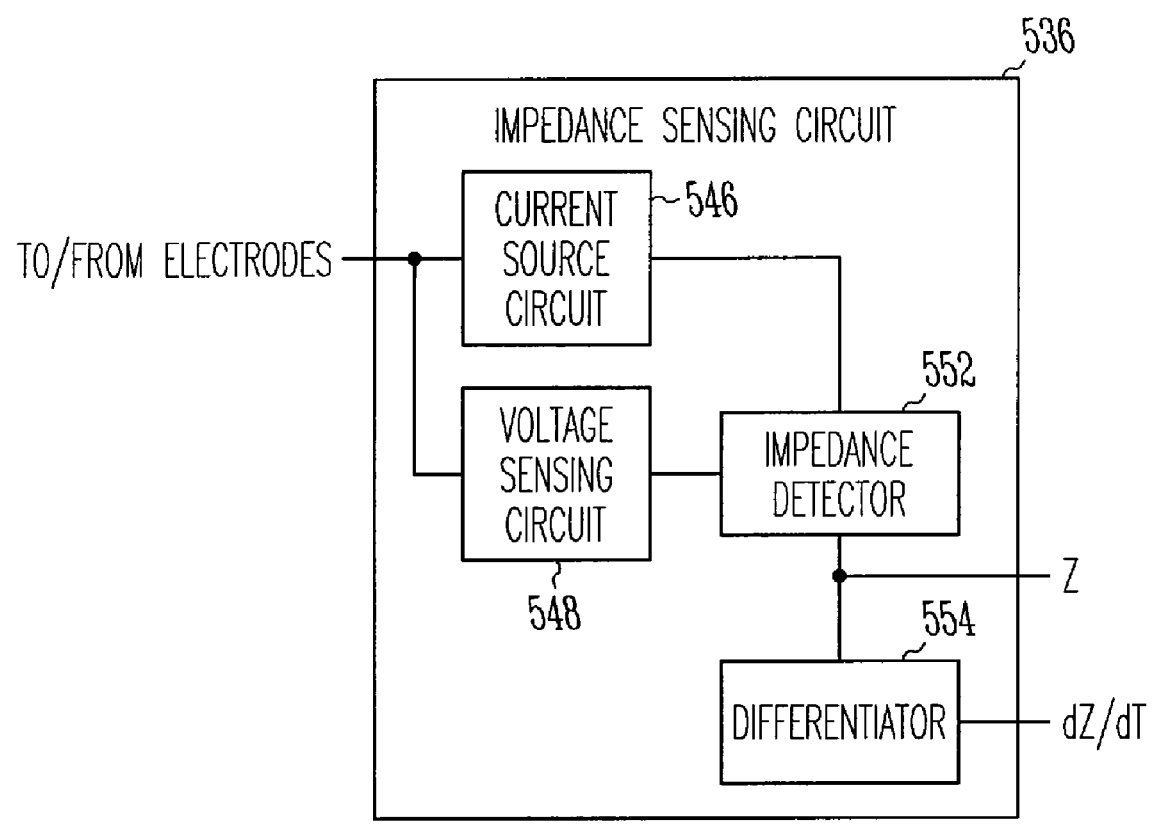
FIG. 5 is a block diagram illustrating an embodiment of an impedance sensing circuit of the implantable medical device.

FIG. 5 is a block diagram illustrating an embodiment of an impedance sensing circuit 536. Impedance sensing circuit 536 is a specific embodiment of impedance sensing circuit 436 and includes a current source circuit 546, a voltage sensing circuit 548, an impedance detector 552, and a differentiator 554.

Current source circuit 546 includes delivers a current through a pair of impedance sensing electrodes. In one embodiment, current source circuit 546 delivers constant current pulses at a frequency between approximately 3 Hz and 500 Hz, with approximately 20 Hz as a specific example. The constant current pulses each have an amplitude between approximately 20 microamperes and 400 microamperes, with approximately 80 microamperes as a specific example, and a pulse width between approximately 10 microseconds and 100 microseconds, with approximately 40 microseconds as a specific example. Voltage sensing circuit 548 senses a voltage across the pair of impedance sensing electrodes and produces a sensed voltage. Impedance detector 552 produces a cardiac local impedance signal (Z) using the sensed voltage. In one embodiment, impedance detector 552 produces the cardiac local impedance signal (Z) as a ratio of the voltage sensed by voltage sensing circuit 548 to the current delivered from current source circuit 546. In another embodiment, impedance detector 552 produces the cardiac local impedance signal (Z) by isolating the signal component indicative of the cardiac local impedance from the voltage sensed by voltage sensing circuit 548, when the current delivered from current source circuit 546 is in the form of constant current pulses. Differentiator 554 produces a cardiac local impedance derivative signal (dZ/dT) that indicates the rate of change in the cardiac local impedance. In one embodiment, differentiator 554 includes a high-pass filter having a cutoff frequency between approximately 0.1 Hz and 1 Hz, with approximately 0.5 Hz being a specific example.

Figure 6:
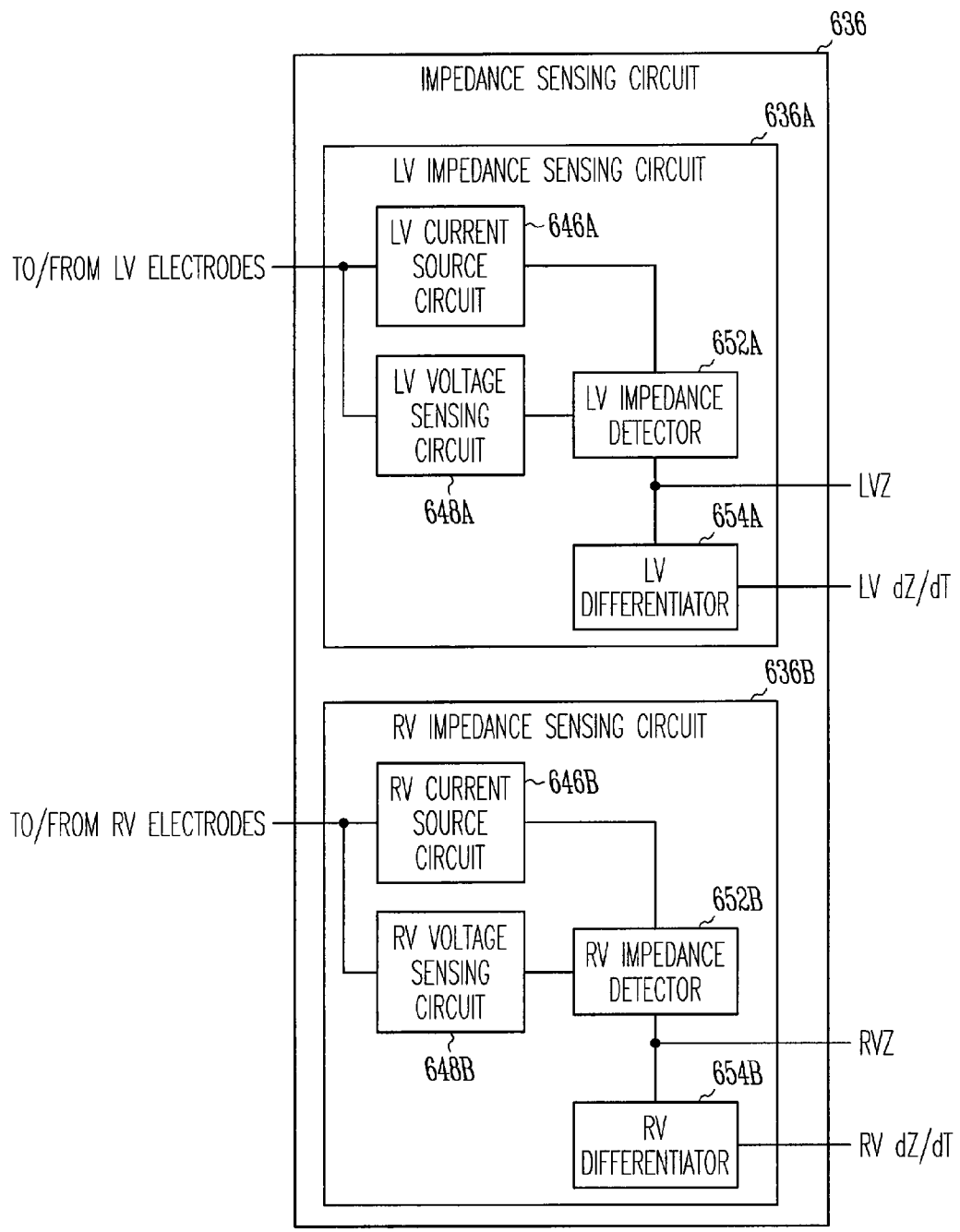
FIG. 6 is a block diagram illustrating another embodiment of the impedance sensing circuit.

FIG. 6 is a block diagram illustrating an embodiment of an impedance sensing circuit 636. Impedance sensing circuit 636 is a specific embodiment of impedance sensing circuit 536 that allows for sensing of multiple cardiac local impedance signals. In the illustrated embodiment, impedance sensing circuit 636 includes two impedance sensing sub-circuits: an LV impedance sensing circuit 636A and an RV impedance sensing circuit 636B sensing. LV impedance sensing circuit 636A produces an LV local impedance signal indicative of an LV local wall motion. RV impedance sensing circuit 636B produces an RV local impedance signal indicative of an RV local wall motion. In other embodiments, impedance sensing circuit 636 includes two or more impedance sensing sub-circuits each sensing a local impedance signal in a cardiac region.

LV impedance sensing module 636A includes an LV current source circuit 646A, an LV voltage sensing circuit 648A, an LV impedance detector 652A, and an LV differentiator 654A. LV current source circuit 646A delivers an LV current through a pair of LV impedance sensing electrodes, such as LV electrodes 128A and 128B. LV voltage sensing circuit 648A senses an LV voltage across the pair of LV impedance sensing electrodes. LV impedance detector 652A produces an LV local impedance signal (LVZ). In one embodiment, LV impedance detector 652A produces the LV local impedance signal (LVZ) as a ratio of the LV voltage to the LV current. In another embodiment, LV impedance detector 652A produces the LV local impedance signal (LVZ) by isolating the signal component indicative of the LV local impedance from the LV voltage, when the LV current is delivered as constant-current pulses. LV differentiator 654A produces an LV local impedance derivative signal (LV dZ/dT), which indicates the rate of change in the LV local impedance.

RV impedance sensing module 636B includes an RV current source circuit 646B, an RV voltage sensing circuit 648B, an RV impedance detector 652B, and an RV differentiator 654B. RV current source circuit 646B delivers an RV current through a pair of RV impedance sensing electrodes, such as RV electrodes 120A and 120B. RV voltage sensing circuit 648B senses an RV voltage across the pair of RV impedance sensing electrodes. RV impedance detector 652B produces an RV local impedance signal (RVZ). In one embodiment, RV impedance detector 652B produces the RV local impedance signal (RVZ) as a ratio of the RV voltage to the RV current. In another embodiment, RV impedance detector 652B produces the RV local impedance signal (RVZ) by isolating the signal component indicative of the RV local impedance from the LV voltage, when the RV current is delivered as constant-current pulses. RV differentiator 654B produces an RV local impedance derivative signal (RV dZ/dT), which indicates the rate of change in the RV local impedance.

Figure 7:
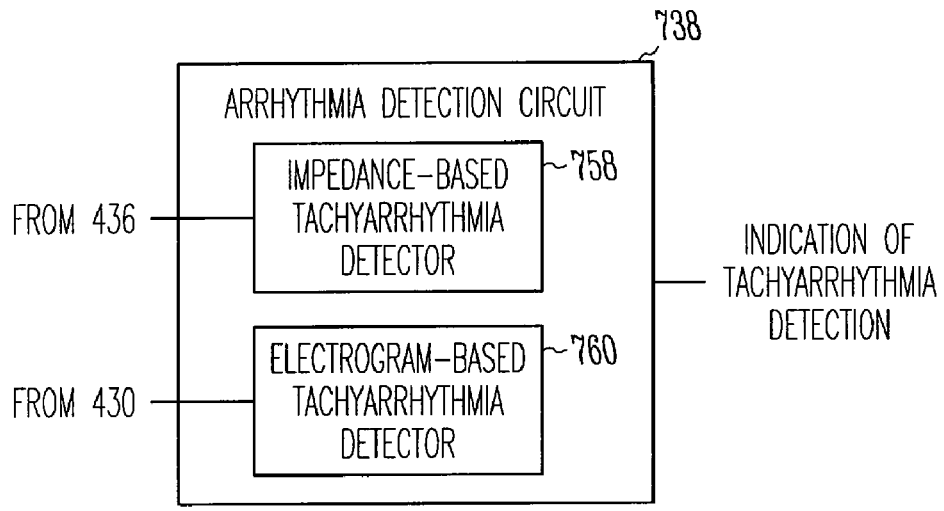
FIG. 7 is a block diagram illustrating an embodiment of an arrhythmia detection circuit of the implantable medical device.

FIG. 7 is a block diagram illustrating an embodiment of an arrhythmia detection circuit 738, which is a specific embodiment of arrhythmia detection circuit 438. In the illustrated embodiment, arrhythmia detection circuit 738 includes an impedance-based tachyarrhythmia detector 758 and an electrogram-based tachyarrhythmia detector 760. Impedance-based tachyarrhythmia detector 758 detects tachyarrhythmia using one or more cardiac local impedance signals. Electrogram-based tachyarrhythmia detector 760 detects tachyarrhythmia using one or more electrograms. In one embodiment, arrhythmia detection circuit 738 detects a predetermined-type tachyarrhythmia using the one or more cardiac local impedance signals and the one or more electrograms. In one embodiment, a detection of the predetermined-type tachyarrhythmia is indicated when impedance-based tachyarrhythmia detector 758 and electrogram-based tachyarrhythmia detector 760 both indicate a detection of the tachyarrhythmia. In another embodiment, a detection of the predetermined-type tachyarrhythmia is indicated using weighted outputs of impedance-based tachyarrhythmia detector 758 and electrogram-based tachyarrhythmia detector 760. In one embodiment, impedance-based tachyarrhythmia detector 758 and electrogram-based tachyarrhythmia detector 760 supplement each other in tachyarrhythmia detection. For example, electrogram-based tachyarrhythmia detector 760 detects a fast heart rate, and impedance-based tachyarrhythmia detector 758 is activated in response to a detection of the fast heart rate. In one embodiment, arrhythmia detection circuit 738 includes only impedance-based tachyarrhythmia detector 758.

Figure 8:
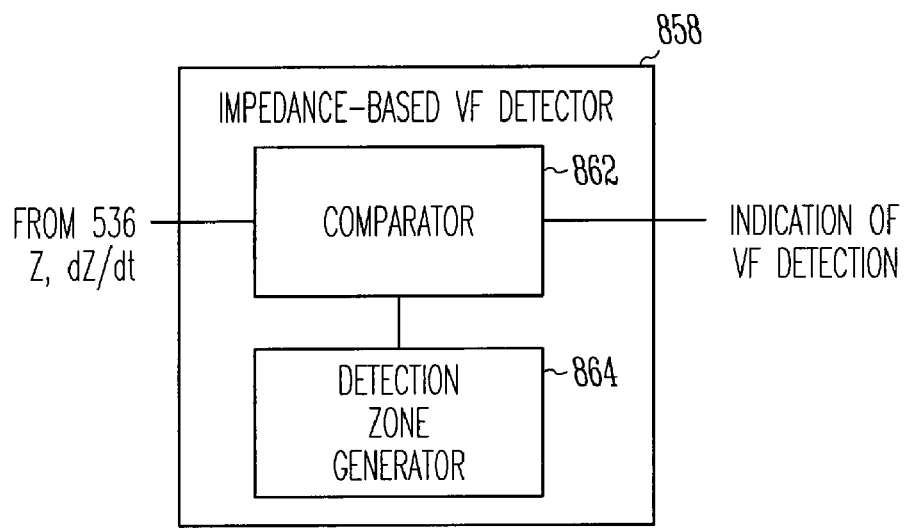
FIG. 8 is a block diagram illustrating an embodiment of an impedance-based VF detector of the arrhythmia detection circuit.

FIG. 8 is a block diagram illustrating an embodiment of an impedance-based VF detector 858. Impedance-based VF detector 858 is a specific embodiment of impedance-based tachyarrhythmia detector 758 and includes a comparator 862 and a detection zone generator 864.

In one embodiment, impedance-based VF detector 858 detects VF using a cardiac local impedance signal (Z). Detection zone generator 864 produces a VF detection zone specified by one or more threshold amplitudes. Comparator 862 has a signal input that receives the cardiac local impedance signal (Z), one or more threshold inputs that receives the one or more threshold amplitudes, and an output that indicates a VF detection when the amplitude of the cardiac local impedance signal (Z) falls into the VF detection zone. In one embodiment, detection zone generator 864 adjusts the VF detection zone based on a trend of the cardiac local impedance signal (Z).

In one embodiment, impedance-based VF detector 858 detects VF using a cardiac local impedance derivative signal (dZ/dT). Detection zone generator 864 produces a VF detection zone specified by one or more threshold amplitudes. Comparator 862 has a signal input that receives the cardiac local impedance derivative signal (dZ/dT), one or more threshold inputs that receives the one or more threshold amplitudes, and an output that indicates a VF detection when the amplitude of the cardiac local impedance derivative signal (dZ/dT) falls into the VF detection zone. In one embodiment, detection zone generator 864 adjusts the VF detection zone based on a trend of the cardiac local impedance derivative signal (dZ/dT).

Figure 9:
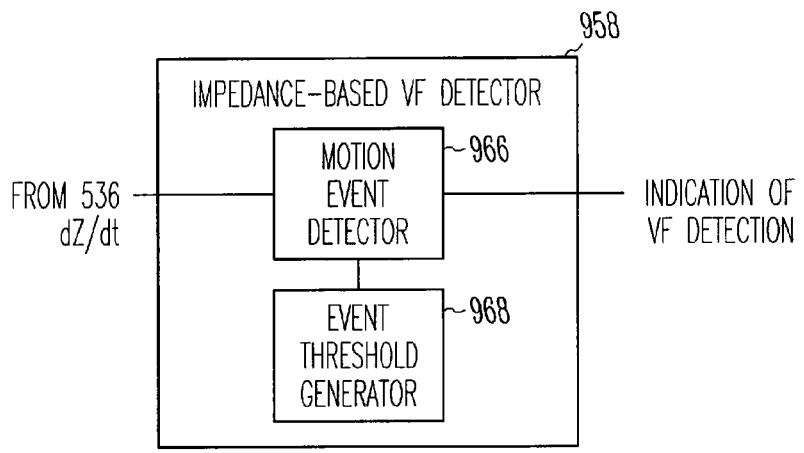
FIG. 9 is a block diagram illustrating another embodiment of the impedance-based VF detector.

FIG. 9 is a block diagram illustrating an embodiment of an impedance-based VF detector 958. Impedance-based VF detector 958 is another specific embodiment of impedance-based tachyarrhythmia detector 758 and includes a motion event detector 966 and an event threshold generator 968 to detect VF.

Motion event detector 966 detects an impedance event from a cardiac local impedance derivative signal (dZ/dT). In one embodiment, the impedance event is representative of a cardiac local wall motion during the systolic phase of each cardiac cycle. Motion event detector 966 indicates a detection of the impedance event when the cardiac local impedance derivative signal (dZ/dT) exceeds an event threshold. Event threshold generator 968 adjusts the event threshold based on a trend of the cardiac local impedance derivative signal (dZ/dT). Impedance-based VF detector 958 detects VF using a pattern of the impedance events (i.e., a pattern of cardiac local wall motion). In one embodiment, impedance-based VF detector 958 indicates a VF detection when the pattern of the impedance events becomes irregular while the heart rate falls into a predetermined VF detection zone.

Figure 10:
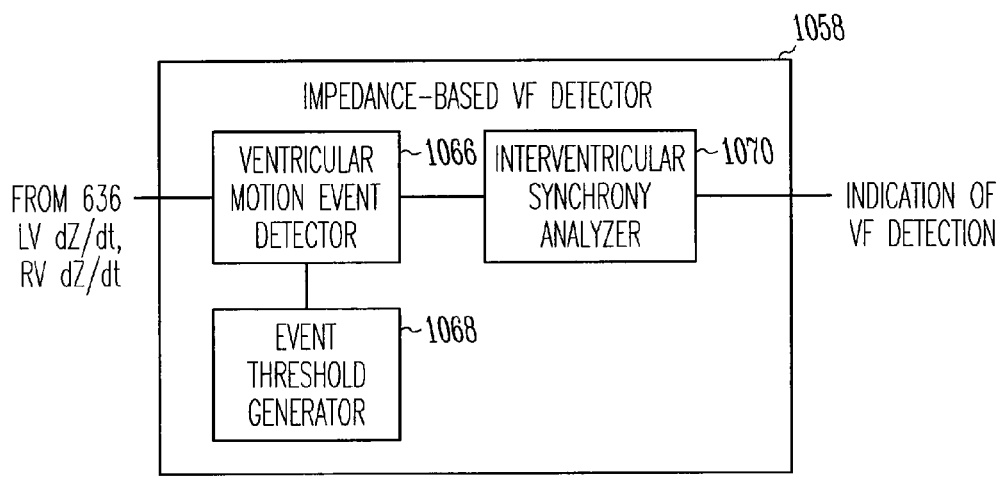
FIG. 10 is a block diagram illustrating another embodiment of the impedance-based VF detector.

FIG. 10 is a block diagram illustrating an embodiment of an impedance-based VF detector 1058. Impedance-based VF detector 1058 is another specific embodiment of impedance-based tachyarrhythmia detector 758 and includes a ventricular motion event detector 1066, an event threshold generator 1068, and an interventricular synchrony analyzer 1070 to detect VF based on whether the LV and RV contract in synchrony. During a normal sinus rhythm or a tachycardia with a regular rhythm, the LV and RV contract in synchrony, and the LV and RV impedance events during each cardiac cycle occur approximately simultaneously, such as shown in FIG. 3. Cardiac disorders such as heart failure may cause a certain degree of dyssynchrony in the LV and RV local wall motions, but during a normal or fast but regular rhythm, the LV and RV contractions generally have a one-to-one relationship and occur within a limited interventricular delay during each cardiac cycle.

Ventricular motion event detector 1066 detects an LV impedance event by comparing the LV local impedance derivative signal (LV dZ/dT) to an LV event threshold, and detects an RV impedance event by comparing the RV local impedance derivative signal (RV dZ/dT) to an RV event threshold. Event threshold generator 1068 adjusts the LV event threshold based on a trend of the LV local impedance derivative signal (LV dZ/dT), and adjusts the RV event threshold based on a trend of the RV local impedance derivative signal (RV dZ/dT). Impedance-based VF detector 1058 detects VF using a pattern of the LV impedance events and the RV impedance events. In the illustrated embodiment, interventricular synchrony analyzer 1070 detects VF by determining whether the pattern of the LV impedance events and the RV impedance events indicates a degree of dyssynchrony between the LV and RV local wall motions that exceeds a predetermined threshold degree. In one embodiment, interventricular synchrony analyzer 1070 indicates a VF detection when the degree of dyssynchrony between the LV and RV local wall motions falls below the predetermined threshold degree while the heart rate falls into a predetermined VF detection zone. In one embodiment, the degree of dyssynchrony between the LV and RV local wall motions is measured by the interventricular delay between the LV and RV local wall motions. Interventricular synchrony analyzer 1070 detects an interventricular delay between the LV impedance event and the RV impedance event during each cardiac cycle and detects VF by comparing the interventricular delay to a predetermined threshold delay. Interventricular synchrony analyzer 1070 indicates a VF detection when the interventricular delay exceeds the predetermined threshold delay while the heart rate falls into a predetermined VF detection zone.

Figure 11:
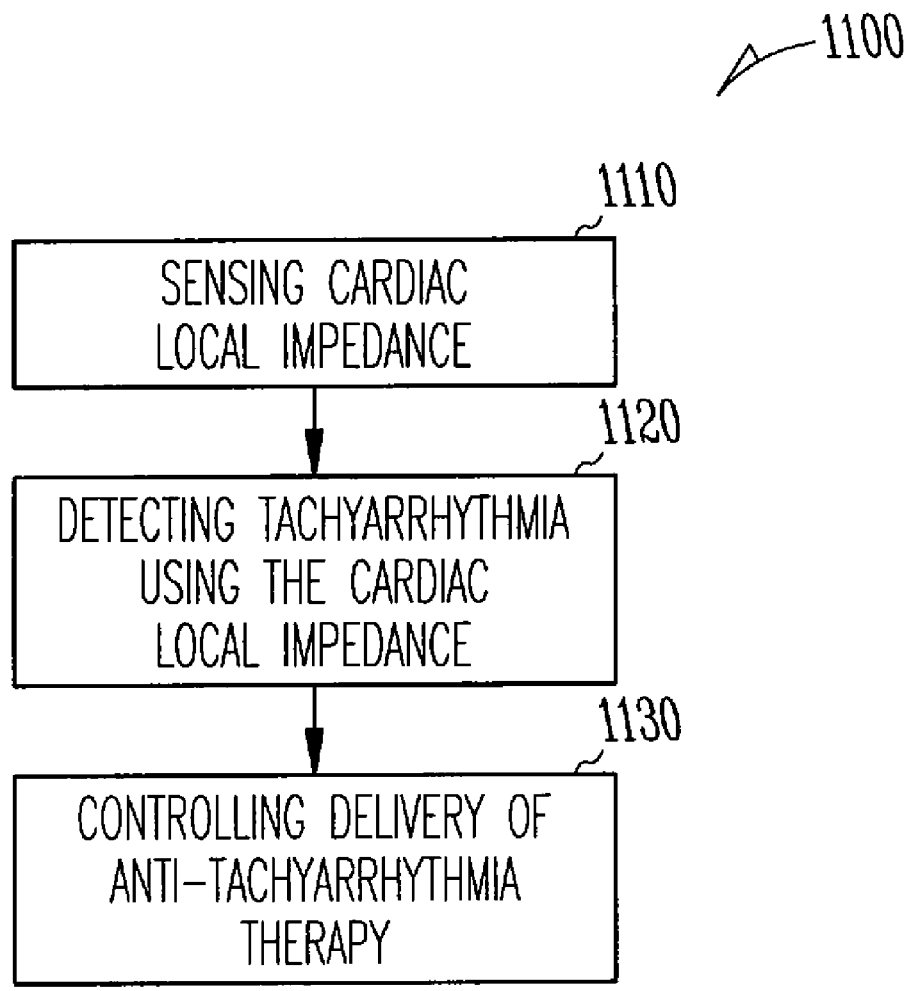
FIG. 11 is a flow chart illustrating an embodiment of a method for detecting tachyarrhythmia using cardiac local impedance.

FIG. 11 is a flow chart illustrating an embodiment of a method 1100 for detecting a tachyarrhythmia using cardiac local impedance. In one embodiment, method 1100 is performed by system 100.

A cardiac local impedance signal is sensed at 1110. The cardiac local impedance signal is sensed using a pair of impedance sensing electrodes placed to sense cardiac local wall motion. In one embodiment, the pair of impedance sensing electrodes includes a pair of bipolar pacing-sensing electrodes at a distal end of an implantable pacing or pacing-defibrillation lead. To sense the cardiac local impedance signal, current pulses are delivered through the pair of impedance sensing electrodes at a frequency between approximately 3 Hz and 500 Hz, with approximately 20 Hz as a specific example. The current pulses each have an amplitude between approximately 20 microamperes and 400 microamperes, with approximately 80 microamperes as a specific example, and a pulse width between approximately 10 microseconds and 100 microseconds, with approximately 40 microseconds as a specific example. The voltage across the pair of impedance sensing electrodes is sensed. In one embodiment, the cardiac local impedance signal (Z) is produced as a ratio of the sensed voltage to the delivered current. In another embodiment, the cardiac local impedance signal (Z) is produced by isolating the signal component indicative of the cardiac local impedance from the sensed voltage, when the delivered current is in the form of constant-current pulses.

In one embodiment, a cardiac local impedance derivative signal (dZ/dT) is produced, for example, by high-pass filtering the cardiac local impedance signal (Z) using a cutoff frequency between approximately 0.1 Hz and 1 Hz, with approximately 0.5 Hz as a specific example.

Tachyarrhythmia is detected using the cardiac local impedance signal at 1120. In one embodiment, tachyarrhythmia is detected using the cardiac local impedance derivative signal. In one embodiment, one or more electrograms are also sensed, and tachyarrhythmia is detected using the cardiac local impedance signal and the one or more electrograms. In one embodiment, a VF detection zone specified by one or more threshold amplitudes is produced, and a VF detection is indicated when the cardiac local impedance signal (Z) or the cardiac local impedance derivative signal (dZ/dT) falls into the VF detection zone. In a specific embodiment, the VF detection zone is adjusted using a trend of the cardiac local impedance signal (Z) or the cardiac local impedance derivative signal (dZ/dT). In one embodiment, an impedance event is detected by comparing the cardiac local impedance derivative signal (dZ/dT) to an event threshold. The impedance event represents a cardiac local wall motion during the systolic phase of each cardiac cycle. The event threshold is adjusted based on a trend of the cardiac local impedance derivative signal (dZ/dT). VF is detected using the pattern of the detected impedance events (i.e., pattern of cardiac local wall motion).

Delivery of an anti-tachyarrhythmia therapy is controlled at 1130. In one embodiment, if VF is detected at 1120, a defibrillation pulse is delivered at 1130.

Figure 12:
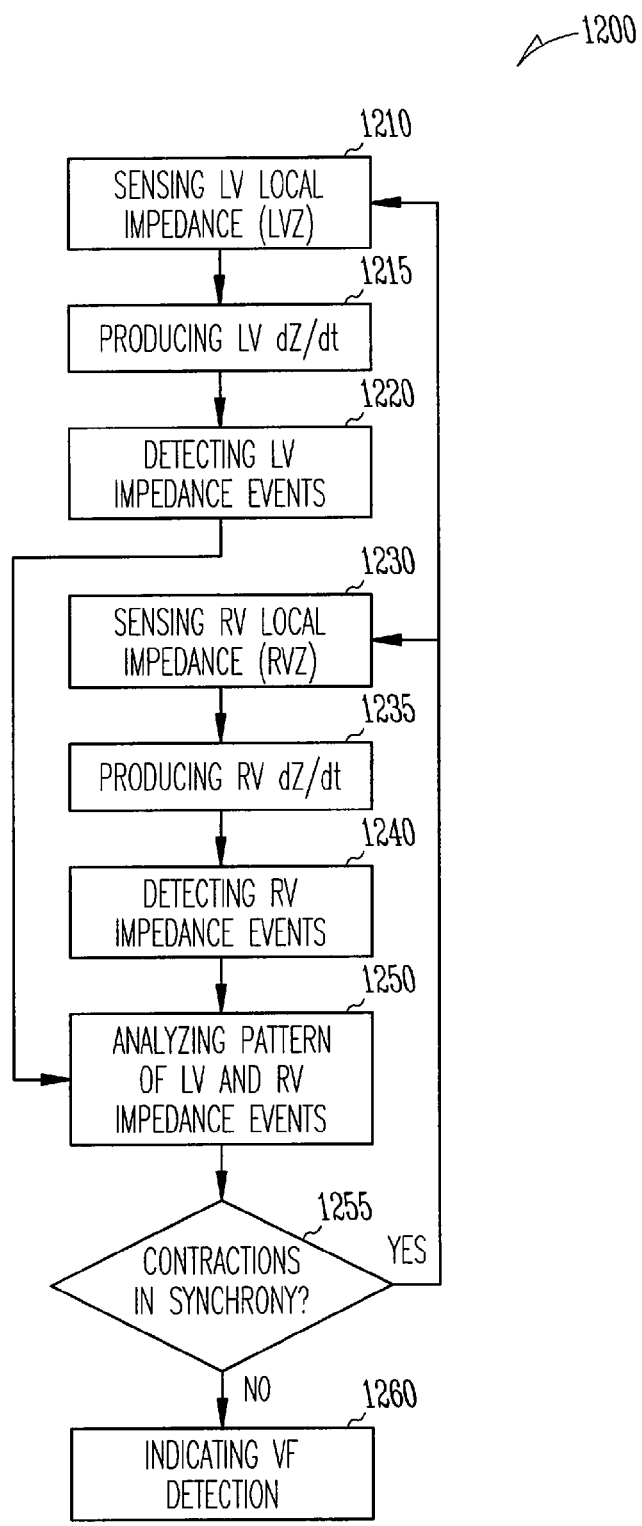
FIG. 12 is a flow chart illustrating an embodiment of a method for detecting VF using cardiac local impedance.

FIG. 12 is a flow chart illustrating an embodiment of a method 1200 for detecting VF using LV and RV local impedance signal. In one embodiment, the method is performed by system 100.

The LV local impedance signal (LVZ) is sensed at 1210. To sense the LV local impedance signal (LVZ), an LV current is delivered through a pair of LV impedance sensing electrodes, and an LV voltage across the pair of LV impedance sensing electrodes is sensed. In one embodiment, the LV local impedance signal (LVZ) is produced as the ratio of the sensed LV voltage to the delivered LV current. In another embodiment, the LV local impedance signal (LVZ) is produced by isolating the signal component indicative of the LV local impedance from the sensed LV voltage, when the delivered LV current is in the form of constant-current pulses. An LV local impedance derivative signal (LV dZ/dT) is produced at 1215. LV impedance events are detected at 1220 by comparing the LV local impedance derivative signal (LV dZ/dT) to an LV event threshold. In one embodiment, the LV impedance events are each representative of an LV local wall motion during the systolic phase of a cardiac cycle. In one embodiment, the LV event threshold is adjusted based on a trend of the LV local impedance derivative signal (LV dZ/dT).

The RV local impedance signal (RVZ) is sensed at 1230. To sense the RV local impedance signal (RVZ), an RV current is delivered through a pair of RV impedance sensing electrodes, and an RV voltage across the pair of RV impedance sensing electrodes is sensed. In one embodiment, the RV local impedance signal (RVZ) is produced as the ratio of the sensed RV voltage to the delivered RV current. In another embodiment, the RV local impedance signal (RVZ) is produced by isolating the signal component indicative of the RV local impedance from the sensed RV voltage, when the delivered RV current is in the form of constant-current pulses. An RV local impedance derivative signal (RV dZ/dT) is produced at 1235. RV impedance events are detected at 1240 by comparing the RV local impedance derivative signal (RV dZ/dT) to an RV event threshold. In one embodiment, the RV impedance events are each representative of an RV local wall motion during the systolic phase of a cardiac cycle. In one embodiment, the RV event threshold is adjusted based on a trend of the RV local impedance derivative signal (RV dZ/dT).

The pattern of the detected LV and RV impedance events is analyzed at 1250. A degree of dyssynchrony between the LV and RV local wall motions is produced based on the pattern. If the degree of dyssynchrony between the LV and RV local wall motions exceeds a predetermined threshold degree (i.e., the LV and RV do not contract in synchrony) at 1255, a VF detection is indicated at 1260. In one embodiment, an interventricular delay between the LV impedance event and the RV impedance event during each cardiac cycle is detected as a measure of the degree of dyssynchrony between the LV and RV local wall motions. The LV and RV contract in synchrony when the LV impedance events and the RV impedance events have approximately a one-to-one relationship and the interventricular delay is within a predetermined limit.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management system for treating a heart, the system comprising:
   an implantable medical device configured to be coupled to an implantable lead including a pair of impedance sensing electrodes configured to be placed in the heart to sense a cardiac local impedance signal indicative of a cardiac local wall motion, the implantable medical device including:
   an impedance sensing circuit adapted to sense the cardiac local impedance signal using the pair of impedance sensing electrodes; and
   an impedance-based tachyarrhythmia detector adapted to detect a predetermined-type tachyarrhythmia using the cardiac local impedance signal, the impedance-based tachyarrhythmia detector including an impedance-based ventricular fibrillation (VF) detector including:
   a detection zone generator adapted to produce a VF detection zone specified by one or more threshold amplitudes; and
   a comparator including a signal input to receive the cardiac local impedance signal, one or more threshold inputs to receive the one or more threshold amplitudes, and an output to indicate a VF detection when the amplitude of the cardiac local impedance signal falls into the VF detection zone.

2. The system of claim 1, wherein the implantable medical device further comprises:
   a cardiac sensing circuit to sense one or more electrograms; and
   an electrogram-based tachyarrhythmia detector adapted to detect the predetermined-type tachyarrhythmia using the one or more electrograms.

3. The system of claim 1, wherein the impedance sensing circuit comprises:
   a current source circuit adapted to deliver a current through the pair of impedance sensing electrodes;
   a voltage sensing circuit adapted to sense a voltage across the pair of impedance sensing electrodes; and
   an impedance detector adapted to produce the cardiac local impedance signal using the sensed voltage.

4. The system of claim 3, wherein the impedance detector is adapted to produce the cardiac local impedance signal as a ratio of the sensed voltage to the delivered current.

5. The system of claim 1, wherein the detection zone generator is adapted to adjust the VF detection zone based on a trend of the cardiac local impedance signal.

6. The system of claim 1, further comprising the first implantable lead, wherein the first implantable lead includes a proximal end configured to be coupled to the implantable medical device, a distal end configured to be placed in the heart and including the pair of impedance sensing electrodes, and an elongate lead body coupled between the proximal end and the distal end.

7. The system of claim 6, wherein a distance between two impedance sensing electrodes of the first pair of impedance sensing electrodes is in a range of approximately 2 millimeters to 40 millimeters.

8. The system of claim 7, wherein the distance between the two impedance sensing electrodes is within approximately 20 millimeters.

9. A cardiac rhythm management system for treating a heart, the system comprising:
   an implantable medical device configured to be coupled to an implantable lead including a pair of impedance sensing electrodes configured to be placed in the heart to sense a cardiac local impedance signal indicative of a cardiac local wall motion, the implantable medical device including:
   an impedance sensing circuit adapted to sense the cardiac local impedance signal using the pair of impedance sensing electrodes, the impedance sensing circuit including a differentiator adapted to produce a cardiac local impedance derivative signal using the cardiac local impedance signal, the cardiac local impedance derivative signal indicative of a rate of change in the cardiac local impedance; and
   an impedance-based tachyarrhythmia detector adapted to detect a predetermined-type tachyarrhythmia using the cardiac local impedance derivative signal, the impedance-based tachyarrhythmia detector including an impedance-based ventricular fibrillation (VF) detector including:
   a detection zone generator adapted to produce a VF detection zone specified by one or more threshold amplitudes; and
   a comparator having a signal input to receive the cardiac local impedance derivative signal, one or more threshold inputs to receive the one or more threshold amplitudes, and an output to indicate a VF detection when the amplitude of the cardiac local impedance derivative signal falls into the VF detection zone.

10. The system of claim 9, wherein the impedance-based VF detector comprises a motion event detector adapted to detect an impedance event in the cardiac local impedance derivative signal, the impedance event representative of a cardiac local wall motion during a systolic phase of each cardiac cycle, the motion event detector adapted to indicate a detection of the impedance event when the cardiac local impedance derivative signal exceeds an event threshold.

11. The system of claim 10, wherein the impedance-based VF detector comprises an event threshold generator adapted to adjust the event threshold based on a trend of the cardiac local impedance derivative signal.

12. The system of claim 9, further comprising the implantable lead, wherein the implantable lead includes a proximal end configured to be coupled to the implantable medical device, a distal end configured to be placed in the heart and including the pair of impedance sensing electrodes, and an elongate lead body coupled between the proximal end and the distal end.

13. The system of claim 12, wherein a distance between two impedance sensing electrodes of the pair of impedance sensing electrodes is in a range of approximately 2 millimeters to 40 millimeters.

14. The system of claim 13, wherein the distance between the two impedance sensing electrodes is within approximately 20 millimeters.

15. A cardiac rhythm management system for treating a heart, the system comprising:

an implantable medical device configured to be coupled to an implantable left ventricular (LV) lead including a pair of LV impedance sensing electrodes configured to be placed on the heart to sense an LV local impedance signal (LVZ) indicative of an LV local wall motion, the implantable medical device including:
an LV impedance sensing circuit adapted to sense the LVZ using the LV impedance sensing electrodes; and
an impedance-based tachyarrhythmia detector adapted to detect a predetermined-type tachyarrhythmia using the LVZ.

16. The system of claim 15, further comprising an implantable right ventricular (RV) lead including a pair of RV impedance sensing electrodes configured to sense an RV local impedance signal (RVZ) indicative of an RV local impedance, and wherein the impedance sensing circuit further comprises an RV impedance sensing circuit adapted to sense the RVZ using the RV impedance sensing electrodes.

17. The system of claim 16, wherein the impedance-based tachyarrhythmia detector is adapted to detect the predetermined-type tachyarrhythmia using the LVZ and the RVZ.

18. The system of claim 16, wherein the impedance sensing circuit further comprises an LV differentiator adapted to produce of an LV local impedance derivative signal (LV dZ/dT) indicative of a rate of change in the LV local impedance and an RV differentiator adapted to produce of an RV local impedance derivative signal (RV dZ/dT) indicative of a rate of change in the RV local impedance, and wherein the impedance-based tachyarrhythmia detector is adapted to detect the predetermined-type tachyarrhythmia using the LV dZ/dT and the RV dZ/dT.

19. The system of claim 18, wherein the impedance-based VF detector comprises a ventricular motion event detector adapted to detect LV impedance events by comparing the LV dZ/dT to an LV event threshold and to detect RV impedance events by comparing the RV dZ/dT to an RV event threshold, the LV impedance events each representative of an LV local wall motion during a systolic phase of a cardiac cycle, the RV impedance events each representative of an RV local wall motion during the systolic phase of the cardiac cycle.

20. The system of claim 19, wherein the impedance-based VF detector comprises an event threshold generator adapted to adjust the LV event threshold based on a trend of the LV dZ/dT and to adjust the RV event threshold based on a trend of the RV dZ/dT.

21. The system of claim 19, wherein the impedance-based VF detector is adapted to detect VF using a pattern of the LV impedance events and the RV impedance events.

22. The system of claim 21, wherein the impedance-based VF detector comprises an interventricular synchrony analyzer adapted to detect VF by determining whether the pattern of the LV impedance events and the RV impedance events indicates a degree of dyssynchrony between the LV and RV local wall motions that exceeds a predetermined threshold degree.

23. The system of claim 15, further comprising the implantable LV lead, wherein the implantable LV lead includes a proximal end configured to be coupled to the implantable medical device, a distal end configured to be placed on the heart and including the pair of LV impedance sensing electrodes, and an elongate lead body coupled between the proximal end and the distal end.

24. The system of claim 23, wherein a distance between two impedance sensing electrodes of the pair of LV impedance sensing electrodes is in a range of approximately 2 millimeters to 40 millimeters.

25. The system of claim 24, wherein the distance between the two impedance sensing electrodes is within approximately 20 millimeters.

* * * * *

UNITED STATES PATENT AND TRADEMARK OFFICE
CERTIFICATE OF CORRECTION

| | | |
|---|---|---|
| PATENT NO. | : 7,890,163 B2 | Page 1 of 1 |
| APPLICATION NO. | : 11/550923 | |
| DATED | : February 15, 2011 | |
| INVENTOR(S) | : Andres Belalcazar | |

It is certified that error appears in the above-identified patent and that said Letters Patent is hereby corrected as shown below:

In column 14, line 2, in Claim 7, after "the" delete "first".

Signed and Sealed this
Tenth Day of May, 2011

David J. Kappos
*Director of the United States Patent and Trademark Office*